United States Patent

Miyashita et al.

Patent Number: 5,189,027
Date of Patent: Feb. 23, 1993

[54] 2-SUBSTITUTED ADENOSINE DERIVATIVES AND PHARMACEUTICAL COMPOSITIONS FOR CIRCULATORY DISEASES

[75] Inventors: Takanori Miyashita, Choshi; Toichi Abiru, Sawara; Yohko Watanabe, Choshi; Toyofumi Yamaguchi, Hachioji; Akira Matsuda, Sapporo, all of Japan

[73] Assignee: Yamasa Shoyu Kabushiki Kaisha, Chiba, Japan

[21] Appl. No.: 799,071

[22] Filed: Nov. 27, 1991

[30] Foreign Application Priority Data

Nov. 30, 1990 [JP] Japan .................. 2-337273
Feb. 28, 1991 [JP] Japan .................. 3-34249

[51] Int. Cl.$^5$ .................. C07H 19/167; A61K 31/70
[52] U.S. Cl. .................. 514/46; 536/27.6; 536/27.3; 536/26.7
[58] Field of Search .................. 514/46; 536/26

[56] References Cited

U.S. PATENT DOCUMENTS 4,956,345  9/1990  Miyasaka et al. .............. 514/46
4,992,427  2/1991  Nair .............................. 514/45

FOREIGN PATENT DOCUMENTS 0219876  4/1987  European Pat. Off. .

OTHER PUBLICATIONS

Matsuda et al., *Nucl. Acids Res. Symp. Ser.*, 16, 97-100 (1985).
Matsuda et al., *Nucl. Acids Res. Symp. Ser.*, 12, 5-8 (1983).
Matsuda et al., *Chem. Pharm. Bull.*, 33(4), 1766-1769 (1985).
Nair et al., "Copper Mediated Reactions in Nucleoside Synthesis," *Tett. Lett.*, 31(6), 807-810 (1990).

*Primary Examiner*—Johnnie R. Brown
*Assistant Examiner*—L. Eric Crane
*Attorney, Agent, or Firm*—Wenderoth, Lind & Ponack

[57] ABSTRACT

Disclosed herein are a novel 2-substituted adenosine derivative having the following formula [I]

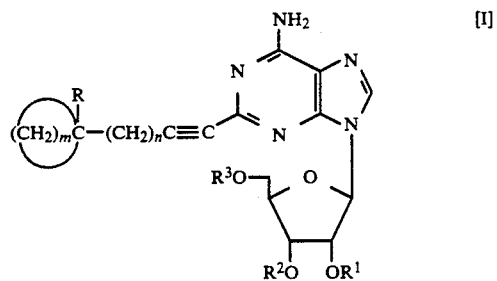

wherein R represents a hydrogen atom or a hydroxyl group, m is an integer of 2 to 7, n is 0 or an integer of 1 to 3, and $R^1$, $R^2$ and $R^3$, which may be the same or different, each independently represent a hydrogen atom, a hydroxy protective group or a phosphoric acid residue, and salts thereof.

The above compounds are excellent in a circulation ameliorating effect such as a vasodepressor activity, and have high selectivity for $A_2$ receptors, but cause less undesirable side effects such as a suppresssive effect on the heart. They are therefore effective when used in pharmaceutical compositions for circulatory diseases.

5 Claims, No Drawings

2-SUBSTITUTED ADENOSINE DERIVATIVES AND PHARMACEUTICAL COMPOSITIONS FOR CIRCULATORY DISEASES

BACKGROUND OF THE INVENTION

The present invention relates to novel 2-substituted adenosine derivatives and pharmaceutical compositions for circulatory diseases comprising the same as an active ingredient.

It has been known that adenosine has potent hypotensive and platelet aggregation inhibitory effects. However, these advantageous effects cannot last for a long period of time. In addition, adenosine gives rise to some undesirable side effects such as a suppressive effect on the heart (a heart-rate reducing effect, etc.) and a central inhibitory effect. It is therefore necessary to solve these problems in order to use adenosine or its derivatives as therapeutic agents for diseases such as hypertension and stenocardia.

To solve the above problems, various 2-substituted adenosine derivatives have been synthesized as described in Chem. Pharm. Bull., 23(4), 759–774 (1975) and Japanese Laid-Open Patent Publication No. 265100/1989. However, even these derivatives cannot provide a satisfactory solution of the above problems, so that they are not practically used as pharmaceuticals as yet.

We have succeeded in synthesis of adenosine derivatives having a specific alkynyl group at the 2 position thereof as reported, for instance, in Chem. Pharm. Bull., 33(4), 1766–1769 (1985), and found that among these derivatives, those compounds having a linear carbon chain as the alkynyl group exhibit a remarkable and lasting vasodepressor activity but have a less adverse effect on the heart rate (see Nucleic Acids Research, Symposium Series No. 16, 97–100 (1985), and Japanese Patent Publications Nos. 33477/1989 and 17526/1990).

The 2-alkynyladenosines having a linear carbon chain have potent and lasting pharmacological effects on circulatory organs and yet entail less serious side effects as compared with other conventional adenosine derivatives. However, there has long been awaited the advent of a compound which is improved in the above advantageous properties, characteristic of the 2-alkynyladenosines.

In recent years, it is reported that a vasodepressor activity, a platelet aggregation inhibitory effect and the like are manifested through $A_2$ adenosine receptors (hereinafter referred to simply as "$A_2$ receptor"), while a suppressive effect on the heart, a central inhibitory effect and the like are manifested through $A_1$ adenosine receptors (hereinafter referred to Simply as "$A_1$ receptor"). For instance, 5'-N-ethylcarboxamideadenosine (NECA) described in Archs. Pharmacodyn., 230, 140–149 (1977) has been known as a compound having a high affinity for $A_2$ receptors and is already employed as a ligand for binding assay (see Mol. Pharmacol., 29, 331–346 (1986)). However, this compound also has a high affinity for $A_1$ receptors so that it tends to give rise to the aforementioned side effects. For this reason, the compound is not utilizable as a therapeutic agent.

Accordingly, adenosine derivatives which have a high affinity for $A_2$ receptors but a low affinity for $A_1$ receptors may be useful as therapeutic or prophylactic agents for circulatory diseases, such as hypertension and ischemic heart or brain diseases.

An object of the present invention is therefore to provide 2-substituted adenosine derivatives which have potent and lasting pharmacological activities such as a vasodepressor activity, coronary vasodilating effect, peripheral vasodilating effect, cerebral circulation ameliorating effect, peripheral circulation ameliorating effect, platelet aggregation inhibitory effect and antiarteriosclerotic effect, have high selectivity for $A_2$ receptors, and yet entail substantially no side effects such as a suppressive effect on the heart and a central inhibitory effect.

SUMMARY OF THE INVENTION

In the process of the development of novel adenosine derivatives and the studies on their pharmacological activities, we have found that specific adenosine derivatives have a high affinity for $A_2$ receptors but a low affinity for $A_1$ receptors, in other words, have high selectivity for $A_2$ receptors, and that these adenosine derivatives are efficacious for circulatory diseases. This invention has been accomplished on the basis of the above finding.

More specifically, the present invention provides 2-substituted adenosine derivatives having the following formula [I] (hereinafter referred to often as "the compound of the present invention"):

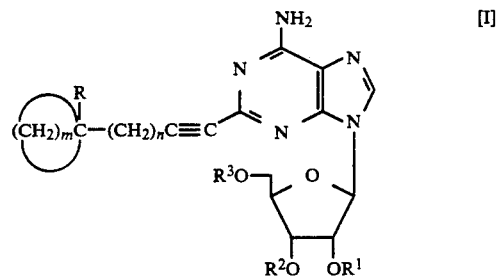

wherein R represents a hydrogen atom or a hydroxyl group, m is an integer of 2 to 7, n is 0 or an integer of 1 to 3, and $R^1$, $R^2$ and $R^3$, which may be the same or different, each independently represent a hydrogen atom, a hydroxy protective group or a phosphoric acid residue, and salts thereof.

The present invention also provides pharmaceutical compositions for circulatory diseases comprising as an active ingredient the 2-substituted adenosine derivatives having the above formula [I] or pharmaceutically acceptable salts thereof.

DETAILED DESCRIPTION OF THE INVENTION

Compound of the Present Invention

In the case where $R^1$, $R^2$ and/or $R^3$ in formula [I] represent/represents hydroxy protective groups, they may be substituents which are usually utilized as hydroxy protective groups in nucleosides, and two or more of them are the same or different from one another. Specific examples of the protective groups include acyl groups such as acetyl, chloroacetyl, dichloroacetyl, trifluoroacetyl, methoxyacetyl, propionyl, n-butyryl, (E)-2-methylbutenoyl, isobutyryl, pentanoyl, benzoyl, o-(dibromomethyl)benzoyl, o-(methoxycarbonyl)benzoyl, p-phenylbenzoyl, 2,4,6-trimethylbenzoyl, p-toluoyl, p-anisoyl, p-chlorobenzoyl, p-nitrobenzoyl and α-naphthoyl; aralkyl groups such as benzyl, phenethyl, 3-phenylpropyl, p-methoxybenzyl, p-nitrobenzyl, o-nitrobenzyl, p-halobenzyl, p-cyanobenzyl, diphenylmethyl, triphenylmethyl (trityl), α- or β-naphthylmethyl and α-naphthyldiphenylmethyl; silyl groups such as trimethylsilyl, triethylsilyl, dimethylisopropylsilyl, isopropyldimethylsilyl, methyl-di-t-butylsilyl, t-butyldimethylsilyl, t-butyldiphenylsilyl, triisopropylsilyl and tetraisopropyldisiloxanyl; alkoxymethyl groups such as methoxymethyl and ethoxymethyl group; and acetal- or ketal-type protective groups such as isopropylidene, ethylidene, propylidene, benzylidene and methoxymethylidene.

In the case where $R^1$, $R^2$ and/or $R^3$ are/is phosphoric acid residues/residue, they may be represented by the following formula [A] or [B]:

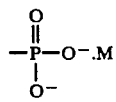   [A]

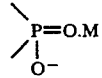   [B]

M in the above formula [A] or [B] represents one or more cations having a positive charge which corresponds to a negative charge of the phosphoric acid residue. Specific examples of the cations include a hydrogen ion, a sodium ion, a potassium ion, a calcium ion, a barium ion, a magnesium ion and an ammonium ion. The phosphoric acid residue represented by formula [A] forms, together with one hydroxyl group in a sugar moiety of the compound of formula [I], a phosphoric ester. The phosphoric acid residue represented by formula [B] forms, together with two hydroxyl groups in a sugar moiety of the compound [I], a cyclic phosphoric ester.

Among the 2-substituted adenosine derivatives of formula [I], those in which $R^1$, $R^2$ and $R^3$ are hydrogen atoms are shown in Tables 1(A) and (B) below.

TABLE 1

| Compound No. | n | m | R | Compound of the Present Invention |
|---|---|---|---|---|
| 1 | 0 | 2 | H | 2-(cyclopropylethynyl)adenosine |
| 2 | 1 | 2 | H | 2-(3-cyclopropyl-1-propynyl)adenosine |
| 3 | 2 | 2 | H | 2-(4-cyclopropyl-1-butynyl)adenosine |
| 4 | 3 | 2 | H | 2-(5-cyclopropyl-1-pentynyl)adenosine |
| 5 | 0 | 2 | OH | 2-[(1-hydroxycyclopropane-1-yl)ethynyl]adenosine |
| 6 | 1 | 2 | OH | 2-[3-(1-hydroxycyclopropane-1-yl)-1-propynyl]adenosine |
| 7 | 2 | 2 | OH | 2-[4-(1-hydroxycyclopropane-1-yl)-1-butynyl]adenosine |
| 8 | 3 | 2 | OH | 2-[5-(1-hydroxycyclopropane-1-yl)-1-pentynyl]adenosine |
| 9 | 0 | 3 | H | 2-(cyclobutylethynyl)adenosine |
| 10 | 1 | 3 | H | 2-(3-cyclobutyl-1-propynyl)adenosine |
| 11 | 2 | 3 | H | 2-(4-cyclobutyl-1-butynyl)adenosine |
| 12 | 3 | 3 | H | 2-(5-cyclobutyl-1-pentynyl)adenosine |
| 13 | 0 | 3 | OH | 2-[(1-hydroxycyclobutane-1-yl)ethynyl]adenosine |
| 14 | 1 | 3 | OH | 2-[3-(1-hydroxycyclobutane-1-yl)-1-propynyl]adenosine |
| 15 | 2 | 3 | OH | 2-[4-(1-hydroxycyclobutane-1-yl)-1-butynyl]adenosine |
| 16 | 3 | 3 | OH | 2-[5-(1-hydroxycyclobutane-1-yl)-1-pentynyl]adenosine |
| 17 | 0 | 4 | H | 2-(cyclopentylethynyl)adenosine |
| 18 | 1 | 4 | H | 2-(3-cyclopentyl-1-propynyl)adenosine |
| 19 | 2 | 4 | H | 2-(4-cyclopentyl-1-butynyl)adenosine |
| 20 | 3 | 4 | H | 2-(5-cyclopentyl-1-pentynyl)adenosine |
| 21 | 0 | 4 | OH | 2-[(1-hydroxycyclopentane-1-yl)ethynyl]adenosine |
| 22 | 1 | 4 | OH | 2-[3-(1-hydroxycyclopentane-1-yl)-1-propynyl]adenosine |
| 23 | 2 | 4 | OH | 2-[4-(1-hydroxycyclopentane-1-yl)-1-butynyl]adenosine |
| 24 | 3 | 4 | OH | 2-[5-(1-hydroxycyclopentane-1-yl)-1-pentynyl]adenosine |
| 25 | 0 | 5 | H | 2-(cyclohexylethynyl)adenosine |
| 26 | 1 | 5 | H | 2-(3-cyclohexyl-1-propynyl)adenosine |
| 27 | 2 | 5 | H | 2-(4-cyclohexyl-1-butynyl)adenosine |
| 28 | 3 | 5 | H | 2-(5-cyclohexyl-1-pentynyl)adenosine |
| 29 | 0 | 5 | OH | 2-[(1-hydroxycyclohexane-1-yl)ethynyl]adenosine |
| 30 | 1 | 5 | OH | 2-[3-(1-hydroxycyclohexane-1-yl)-1-propynyl]adenosine |
| 31 | 2 | 5 | OH | 2-[4-(1-hydroxycyclohexane-1-yl)-1-butynyl]adenosine |
| 32 | 3 | 5 | OH | 2-[5-(1-hydroxycyclohexane-1-yl)-1-pentynyl]adenosine |
| 33 | 0 | 6 | H | 2-(cycloheptylethynyl)adenosine |
| 34 | 1 | 6 | H | 2-(3-cycloheptyl-1-propynyl)adenosine |
| 35 | 2 | 6 | H | 2-(4-cycloheptyl-1-butynyl)adenosine |
| 36 | 3 | 6 | H | 2-(5-cycloheptyl-1-pentynyl)adenosine |
| 37 | 0 | 6 | OH | 2-[(1-hydroxycycloheptane-1-yl)ethynyl]adenosine |
| 38 | 1 | 6 | OH | 2-[3-(1-hydroxycycloheptane-1-yl)-1-propynyl]adenosine |
| 39 | 2 | 6 | OH | 2-[4-(1-hydroxycycloheptane-1-yl)-1-butynyl]adenosine |
| 40 | 3 | 6 | OH | 2-[5-(1-hydroxycycloheptane-1-yl)-1-pentynyl]adenosine |
| 41 | 0 | 7 | H | 2-(cyclooctylethynyl)adenosine |
| 42 | 1 | 7 | H | 2-(3-cyclooctyl-1-propynyl)adenosine |
| 43 | 2 | 7 | H | 2-(4-cyclooctyl-1-butynyl)adenosine |
| 44 | 3 | 7 | H | 2-(5-cyclooctyl-1-pentynyl)adenosine |
| 45 | 0 | 7 | OH | 2-[(1-hydroxycyclooctane-1-yl)ethynyl]adenosine |
| 46 | 1 | 7 | OH | 2-[3-(1-hydroxycyclooctane-1-yl)-1-propynyl]adenosine |
| 47 | 2 | 7 | OH | 2-[4-(1-hydroxycyclooctane-1-yl)-1-butynyl]adenosine |
| 48 | 3 | 7 | OH | 2-[5-(1-hydroxycyclooctane-1-yl)-1-pentynyl]adenosine |

As the 2-substituted adenosine derivatives having formula [I] in which $R^1$, $R^2$ and $R^3$ each independently represent a substituent other than a hydrogen atom, 2',3',5'-tri-O-acyl derivatives, 5'-O-acyl derivatives, 5'-O-aralkyl derivatives, 3'-O-aralkyl derivatives, 5'-phosphoric esters and cyclic 3',5'-phosphoric esters of the compounds enumerated in Tables 1(A) and (B) can be mentioned.

The adenosine derivatives having formula [I] can be in free form or as salts. Examples of the salts include acid addition salts such as inorganic acid salts, for instance, hydrochlorides, sulfates and hydrobromides, and organic salts, for instance, oxalates, citrates and malates; alkali metal salts such as a sodium salt and a potassium salt; alkaline earth metal salts such as a calcium salt, a barium salt and a magnesium salt; and ammonium salts. Of these, pharmaceutically acceptable salts such as hydrochloride, oxalate, citrate, malate and sodium salts are preferred.

Production of the Compounds of the Present Invention

Synthesis Process 1

The compound of the present invention can be synthesized by reacting (cross-coupling) a 2-halogenoadenosine derivative having the following formula [II] (hereinafter referred to often as "the starting compound"):

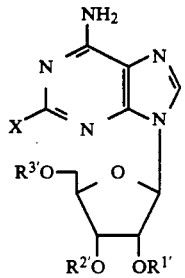

[II]

wherein $R^{1'}$, $R^{2'}$ and $R^{3'}$ each independently represent a hydrogen atom, a hydroxy protective group which is the same as enumerated previously for $R^1$, $R^2$ and $R^3$, or a phosphoric acid residue which is the same as enumerated previously for $R^1$, $R^2$ and $R^3$, and X represents iodine or bromine, with an acetylene compound having the following formula [III]:

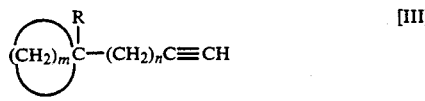

[III]

wherein m, n, and R are as defined before, in a solvent in the presence of a palladium catalyst and a copper compound. After the reaction is completed, the hydroxy protective group in the sugar moiety is eliminated, or a protective group or a phosphoric acid residue is introduced on the hydroxyl group in the sugar moiety, if necessary. The cross-coupling reaction can be carried out in accordance with a known method for synthesizing 2-alkynyladenosines (see Japanese Patent Publications Nos. 33477/1989 and 17526/1990).

It is required to choose an acetylene compound [III] having the numbers m and n and the substituent R suitable for a desired compound of the present invention.

Examples of the solvent usable in the reaction include basic solvents such as triethylamine, tributylamine, N,N-diisopropylethylamine, trioctylamine, N,N,N',N'-tetramethyl-1,8-naphthalenediamine, dimethylaniline, diethylaniline and pyridine, which may be employed singly, or solvent mixtures of a non-protonic polar solvent such as acetonitrile, N,N-dimethylformamide (DMF), dimethyl sulfoxide (DMSO), N,N-dimethylacetamide, tetrahydrofuran (THF) or 1,4-dioxane and the above basic solvent.

Examples of preferred palladium catalysts include bis(acetonitrile)palladium dichloride, bis(triphenylphosphine)palladium dichloride, bis(benzonitrile)palladium dichloride, tetrakis(triphenylphosphine) palladium, and bis(triphenylphosphine)palladium diacetate. A compound which is simply obtainable by separately adding palladium chloride or palladium diacetate and triphenylphosphine to the reaction solution can be used as it is as bis(triphenylphosphine)palladium dichloride or bis(triphenylphosphine)palladium diacetate.

The palladium catalyst is employed in a so-called catalytic amount of approximately 0.001 to 0.1 mol for 1 mol of the starting compound represented by formula [II].

In addition to the palladium catalyst, a copper compound is added to the reaction solution to accelerate the cross-coupling reaction. For instance, approximately 0.06–0.1 mol of a copper halide such as cuprous iodide or cuprous bromide is added to the reaction solution for 1 mol of the starting compound [II].

The starting compound [II] can be reacted with the acetylene compound [III] in the presence of the palladium catalyst and the copper compound at a temperature between 10° C. and 120° C. for 1 to 100 hours. In this reaction, 1 to 2 mol of the acetylene compound is used for 1 mol of the starting compound.

After the cross-coupling reaction is completed, the compound synthesized is isolated and purified by a conventional isolation and purification method applicable to nucleosides, such as adsorption chromatography or recrystallization. If necessary, it can be possible to remove the copper compound from the reaction solution by a treatment with hydrogen sulfide, by extraction and distribution using a mixture of an organic solvent and water, or by a combination thereof.

The hydroxy protective group can be removed by a conventional method. For instance, when the protective group is of the acetal or ketal type, it can be removed by means of hydrolysis using an acid such as trifluoroacetate, trichloroacetate, acetic acid, formic acid, sulfuric acid or hydrochloric acid. In the case where the protective group is a silyl group, it can be removed by a treatment with an acid such as trifluoroacetate, trichloroacetate, tosylic acid, sulfuric acid or hydrochloric acid, tetrabutylammonium fluoride, a pyridine hydrogenfluoride salt or ammonium fluoride, which is carried out in a proper solvent such as THF, DMSO, acetonitrile or 1,4-dioxane. When the protective group is an acyl group, it can be removed by means of hydrolysis with methanolic ammonia, concentrated aqueous ammonia, sodium methoxide, sodium ethoxide, sodium hydroxide or potassium hydroxide. The compound [I] having hydrogen atoms as $R^1$, $R^2$ and $R^3$ can thus be obtained from the compound having formula [I] in which $R^1$, $R^2$ and $R^3$ each represent a protective group.

The compound having formula [I] in which $R^1$, $R^2$ and $R^3$ each independently represent a protective group or a phosphoric acid residue can be synthesized by choosing a compound having formula [II] in which $R^{1'}$, $R^{2'}$ and $R^{3'}$ each represent a protective group or a phosphoric acid residue corresponding to $R^1$, $R^2$ and $R^3$, respectively, as the starting compound, and subjecting it to the above-described cross-coupling reaction.

It is also possible to introduce, by a conventional method, a protective group on the 2', 3' and/or 5' position of a preliminarily synthesized compound having formula [I] in which $R^1$, $R^2$ and $R^3$ each represent a hydrogen atom. For example, a reactive derivative having a protective group to be introduced (a halide (such as a bromide, a chloride or an iodide) thereof when the protective group to be introduced is aralkyl or silyl, and an acid anhydride, an activated ester or a halide (such as a bromide, a chloride or an iodide) of the corresponding carboxylic acid when the protective group is acyl) is reacted with the compound [I] having hydrogen atoms as $R^1$, $R^2$ and $R^3$ in a proper solvent such as pyridine, dioxane, THF, acetonitrile, chloroform, dichloromethane, methanol, ethanol or water, whereby the desired protective group can be introduced into the compound. The reaction can be accelerated by adding to the reaction system sodium hydride or the like when an aralkyl halide is used to introduce aralkyl; imidazole or the like when a silyl halide is used to introduce silyl; and a tertiary amine such as triethylamine, an organic base such as pyridine, picoline or dimethylaminopyridine, an alkali metal hydroxide, or an alkali metal carbonate when an acyl halide or an acid anhydride of a carboxylic acid is used to introduce acyl.

Furthermore, it is possible to introduce, by a conventional method, a phosphoric acid residue on the 2', 3' and/or 5' position of the preliminarily synthesized compound [I] having hydrogen atoms as $R^1$, $R^2$ and $R^3$. In this case, protective groups are first introduced on the positions in the sugar moiety of the compound [I], other than the positions on which the phosphoric acid residues are intended to be introduced, and then a phosphorylating agent such as phosphorus oxychloride is reacted therewith. The phosphoric acid residues can thus be introduced on the desired positions.

Shown below are the typical synthesis schemes of the compounds having formula [I] which are 2',3',5'-tri-O-acyl derivatives, 5'-O-acyl derivatives, 5'-O-aralkyl derivatives, 3'-O-aralkyl derivatives or 5'-phosphoric esters.

2',3',5'-Tri-O-Acyl Derivative

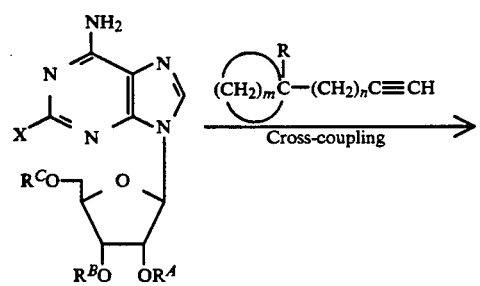
(1)

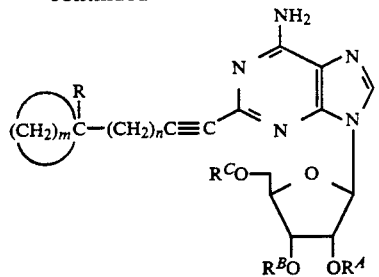

wherein m, n, R and X are as defined before, and $R^A$, $R^B$ and $R^C$ are acyl which corresponds to $R^1$, $R^2$ and $R^3$ in formula [I], or $R^{1'}$, $R^{2'}$ and $R^{3'}$ in formula [II].

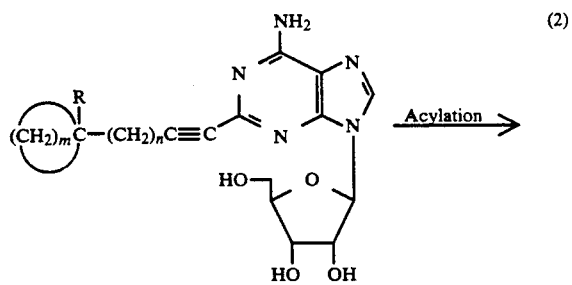
(2)

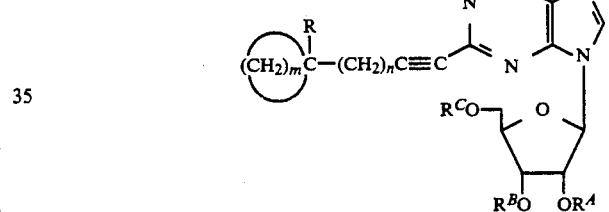

wherein m, n, R, $R^A$, $R^B$ and $R^C$ are as defined above.

5'-O-Acyl Derivative

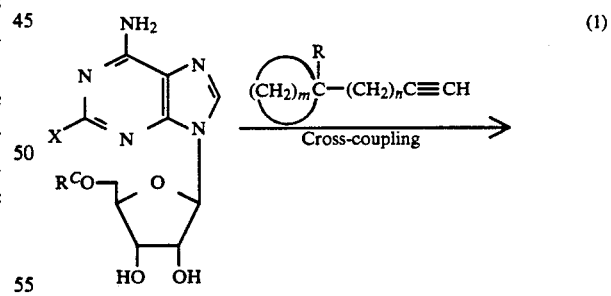
(1)

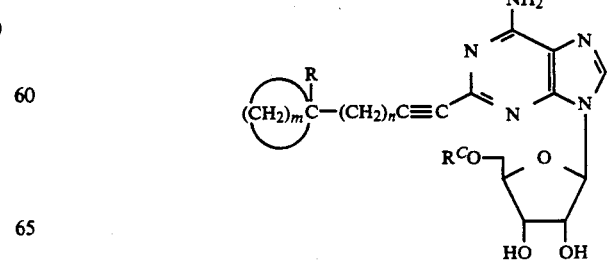

wherein m, n, R, $R^C$ and X are as defined above.

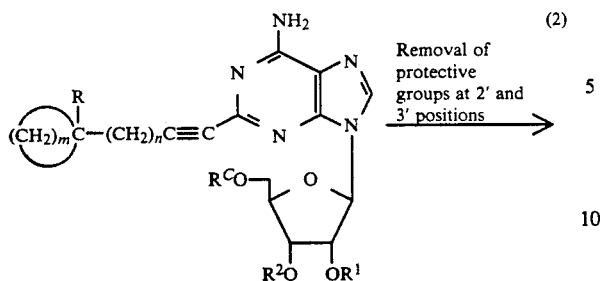
(2)

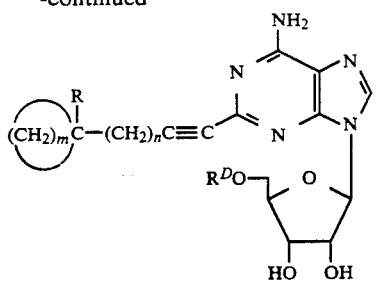
-continued

Removal of protective groups at 2' and 3' positions → wherein m, n, R, $R^1$, $R^2$ and $R^D$ are as defined above.

3'-O-Aralkyl Derivative

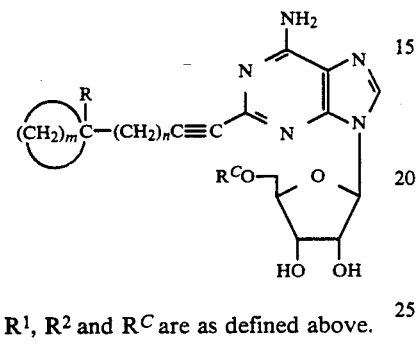

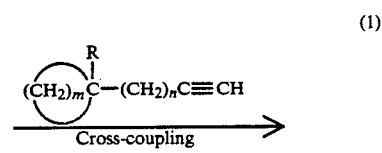
(1)

Cross-coupling → wherein m, n, R, $R^1$, $R^2$ and $R^C$ are as defined above.

5'-O-Aralkyl Derivative

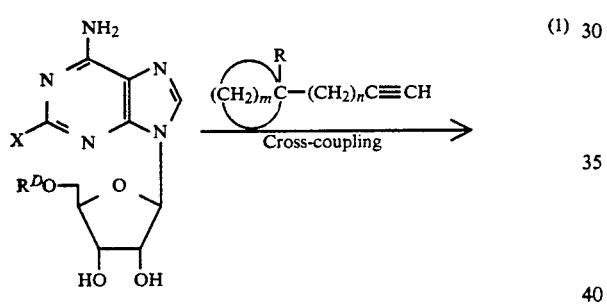
(1)

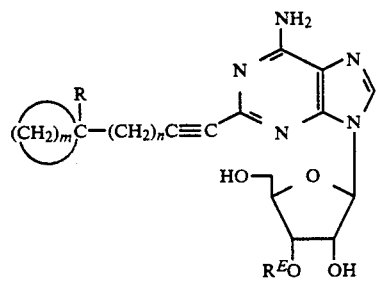

Cross-coupling → wherein m, n, R and X are as defined above, and $R^E$ is aralkyl which corresponds to $R^2$ in formula [I], or $R^{2'}$ in formula [II].

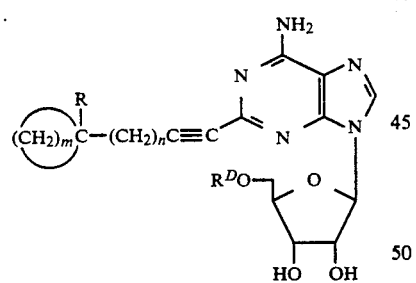

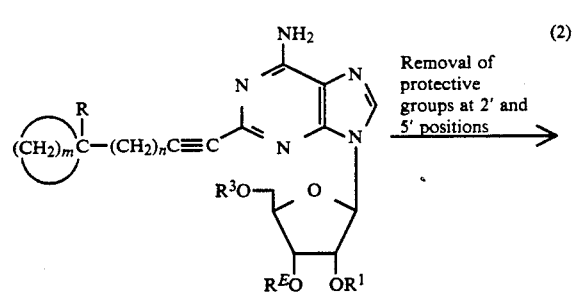
(2)

Removal of protective groups at 2' and 5' positions → wherein m, n, R and X are as defined above, and $R^D$ is aralkyl which corresponds to $R^3$ in formula [I], or $R^{3'}$ in formula [II].

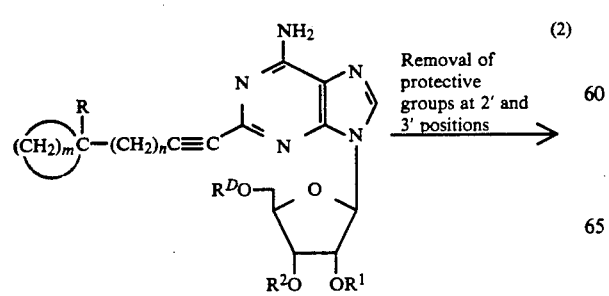
(2)

Removal of protective groups at 2' and 3' positions →

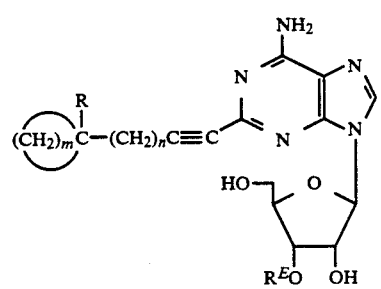

wherein m, n, R, $R^1$, $R^3$ and $R^E$ are as defined above.

5'-Phosphoric Acid Ester

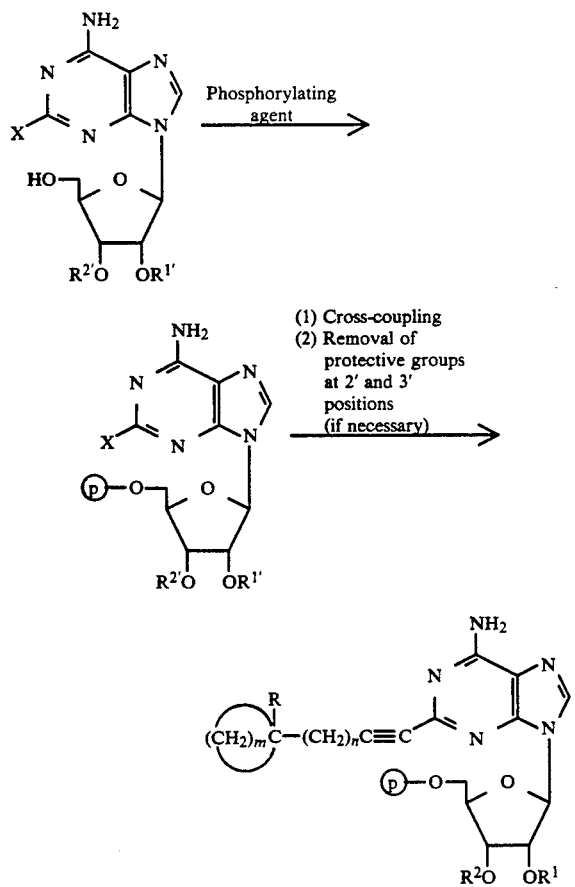

wherein m, n, R and X are as defined above, $R^1$ and $R^2$ each independently represent a hydrogen atom or a hydroxy protective group, $R^{1'}$ and $R^{2'}$ each represent the same hydroxy protective group as is represented by $R^1$ and $R^2$, and represents the aformentioned formula [A].

Synthesis Process 2

The compounds of the present invention having formula [I] can also be synthesized by a method other than the above-described method. For instance, the following synthesis method (see WO 90/15812) can be adopted.

First, a compound having formula [IV]:

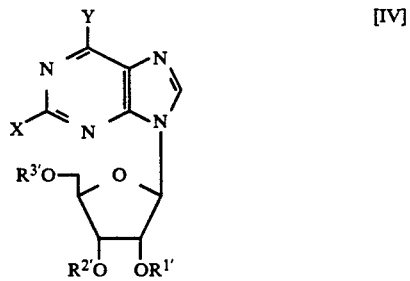

wherein $R^{1'}$, $R^{2'}$, $R^{3'}$ and X are as defined above, and Y represents a leaving group, which is a functional group having low reactivity with an acetylene compound and readily replaceable with an amino group when reacted with an aminating agent, for instance, arylsulfonyloxy such as benzenesulfonyloxy, p-toluenesulfonyloxy, mesitylenesulfonyloxy or 2,4,6-triisopropylbenzenesulfonyloxy, or a chlorine atom, is reacted (cross-coupled) with an acetylene compound having the above-described formula [III] in a reaction solvent in the presence of the aforementioned palladium catalyst, thereby obtaining an intermediate having the following formula [V]:

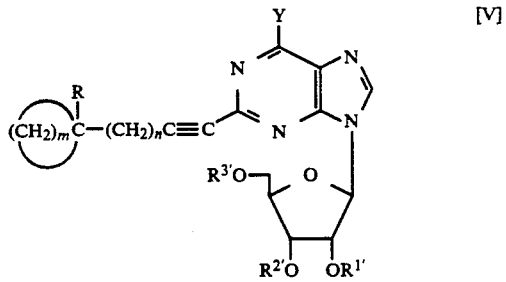

wherein m, n, R, $R^{1'}$, $R^{2'}$, $R^{3'}$ and Y are as defined above.

The above cross-coupling reaction can be carried out basically in the same manner and under the same conditions as in Synthesis Process 1. However, it is not necessary to add a copper compound in the reaction solution. When a copper compound is employed, it is enough to add to the reaction solution such an extremely small amount of copper compound as approximately from 0.001 to 0.05 mol per 1 mol of the compound having formula [IV].

After the reaction is completed, the intermediate [V] is isolated and purified by a conventional isolation and purification method applicable to nucleosides, such as adsorption chromatography and recrystallization. In the case where a copper compound has been employed, the reaction solution is further subjected to a treatment such as extraction and distribution using a solvent mixture of an organic solvent and water to remove the copper compound therefrom. The thus treated intermediate is then subjected to the following amination process for the preparation of the compound of the present invention.

The intermediate [V] is reacted with an aminating agent, and, if necessary, the protective group is removed from the resulting compound, whereby the compound having formula [I] according to the present invention can be obtained.

Examples of the aminating agent usable in the above process include liquid ammonia, alcoholic ammonias such as methanolic ammonia and ethanolic ammonia, and organic solvents, such as acetonitrile, 1,2-dimethoxyethane, 1,4-dioxane and THF, mixed with aqueous ammonia.

The intermediate and the aminating agent can be reacted with each other at a temperature between room temperature and 100° C. for 2 hours to 2 weeks.

After the reaction is completed, the protective group is removed from the compound obtained, if necessary, and the resulting compound is then subjected to a conventional isolation and purification process, thereby obtaining the compound of the present invention.

In the case where the protective group is acyl, the group is removed concurrently with the reaction between the intermediate [V] and the aminating agent. Therefore, a compound having formula [I] in which $R^1$, $R^2$ and $R^3$ each represent a hydrogen atom can be obtained without requiring removal of the acyl after completion of the reaction between the intermediate and the aminating agent.

To synthesize the compound having formula [I] in which $R^1$, $R^2$ and $R^3$ each represent a protective group or a phosphoric acid residue in accordance with Synthesis Process 2, it is preferable to introduce a desired protective group or phosphoric acid residue on the 2′, 3′ and/or 5′ position of a preliminarily synthesized compound having formula [I] in which $R^1$, $R^2$ and $R^3$ each represent a hydrogen atom.

Utility of the Compounds of the Present Invention

Pharmaceutical compositions comprising as an active ingredient the compound of the present invention or its pharmaceutically acceptable salt (which are collectively referred to as "the compound of the present invention" in the following explanation of the pharmaceutical preparations) can be used for the purposes of prophylaxis or therapy of circulatory diseases such as hypertension and ischemic diseases (e.g., ischemic heart diseases, ischemic brain diseases, etc.) in mammals including humans.

The compounds of the present invention can be administered orally or parenterally together with conventional pharmaceutically acceptable carriers for prophylaxis or therapy of the above-described circulatory diseases.

The compounds of the present invention can be made into solid form preparations such as powders, granules, capsules and tablets, and liquid form preparations such as syrups and elixirs, which are suitable for oral administration. Further, they can also be made into injections, rectally applicable preparations, ointments and inhalants, which are suitable for parenteral administration. These preparations can be prepared by a conventional method, adding pharmaceutically acceptable additives to the compounds of the present invention. Moreover, they can also be formed into sustained release preparations in accordance with a known technique.

The solid form preparations for oral administration can be prepared in the following manners.

A powder can be prepared by mixing the compound of the present invention with an excipient such as lactose, starch, crystalline cellulose, calcium lactate, calcium monohydrogenphosphate, magnesium aluminometasilicate or silicic anhydride. To prepare a granule, the above-obtained powder, a binding agent such as refined sugar, hydroxypropyl cellulose or polyvinylpyrrolidone, and a disintegrating agent such as carboxymethyl cellulose or carboxymethyl cellulose calcium are mixed, and the resulting mixture is subjected to wet or dry granulation. A tablet can be prepared by compressing the above-obtained powder or granule, or a mixture of the powder or granule and a lubricant such as magnesium stearate or talc. An enteric-coated preparation can be prepared by coating the above granule or tablet with an enteric base such as hydroxypropylmethylcellulose phthalate or a methyl methacrylate copolymer. A sustained release preparation can be prepared by coating the above granule or tablet with ethyl cellulose, carnauba wax or a hydrogenated oil. To prepare a capsulated preparation, the above powder or granule is charged into a hard capsule, or the compound of the present invention is first dissolved in glycerol, polyethylene glycol, sesame oil or olive oil and then coated with a gelatin film to give a soft capsule.

The liquid preparations for oral administration can be prepared in the following manners.

A clear syrup can be prepared by dissolving the compound of the present invention and a sweetener such as refined sugar, sorbitol or glycerol in water. An elixir can be prepared by further adding an essential oil or ethanol to the above-obtained syrup. An emulsion or suspension can be prepared by adding gum arabic, tragacanth gum, polysorbate 80 or sodium carboxymethyl cellulose to the above syrup. These liquid preparations may also contain flavoring agents, colorants, preservatives and the like, if desired.

To prepare an injection, the compound of the present invention is dissolved in distilled water for injection, if necessary, together with a pH adjusting agent such as hydrochloric acid, sodium hydroxide, lactic acid, sodium lactate, sodium monohydrogenphosphate or sodium dihydrogenphosphate, and an isotonizing agent such as sodium chloride or glucose. The resulting solution is aseptically filtered, and then placed into an ampoule. Further, an injection which should be dissolved on use can be prepared by mixing the above solution with mannitol, dextrin, cyclodextrin or gelatin, and lyophilizing the resulting mixture under vacuum. An emulsion-type injection can be prepared by adding an emulsifier such as lecithin, polysorbate 80 or polyoxyethylenehydrogenated castor oil to the compound of the present invention, and emulsifying the resulting mixture in water.

To prepare a rectally applicable preparation, the compound of the present invention is melted by heating together with a suppository base such as tri-, di- or mono-glyceride of cacao fatty acid or polyethylene glycol, poured into a mold and then cooled. Alternatively, the compound of the present invention is dissolved into polyethylene glycol or soybean oil, and the resulting solution is coated with a gelatin film.

To prepare a preparation for external application, the compound of the present invention is added to white vaseline, beeswax, liquid paraffin or polyethylene glycol, and the mixture is kneaded, if necessary, under heat to give an ointment, or it is kneaded with an adhesive such as rosin or an alkyl acrylate polymer, and then spread over a nonwoven fabric made of, for instance, polyethylene to give a tape preparation.

An aerosol-type inhalant can be prepared by dissolving or dispersing the compound of the present invention in a propellant such as flon gas, followed by charging into a pressure vessel.

The dosage of the compound of the present invention depends on the age and body weight of a patient and the conditions of disease. However, in general, approximately 0.1 mg to 100 mg of the compound is administered per day per individual, desirably at one time or several times.

The compounds of the present invention have a high affinity for $A_2$ receptors, but have a low affinity for $A_1$ receptors. In other words, they have extremely high selectivity for $A_2$ receptors.

Moreover, the compounds of the present invention have a remarkable vasodepressor activity, but have little suppressive effect on the heart. Therefore, they are useful as therapeutic or prophylactic agents for circulatory diseases, such as hypertension and ischemic diseases (e.g., ischemic heart diseases, ischemic brain diseases, etc.).

The foregoing effects of the compounds of the present invention will now be specifically explained with reference to in vitro and in vivo tests in terms of the pharmacological activities.

TEST 1

Affinity for Adenosine Receptors

The affinity of the compounds of the present invention for adenosine receptors was evaluated in substantially the same manner as is described in R. F. Bruns et al., Mol. Pharmacol., 29, 331-346 (1986); R. F. Bruns et al., Proc. Natl. Acad. Sci., U.S.A., 77, 5547 (1980); and Japanese Laid-Open Patent Publications Nos. 201196/1988 and 111996/1987.

More specifically, the affinity of the test compound for $A_1$ receptors was evaluated using Wister rat brain membranes. The affinity constant (Ki) showing the affinity for $A_1$ receptors was obtained from the concentration of the test compound which can substitute 50% of the specific binding of 2.5 nM [$^3$H]-$N^6$-cyclohexyladenosine ([$^3$H]-CHA) to the brain membranes. The affinity of the test compound for $A_2$ receptors was also evaluated using Wister rat striatal membranes. The affinity constant (Ki) showing the affinity for $A_2$ receptors was obtained from the concentration of the test compound which can substitute 50% of the specific binding of 5 nM [$^3$H]-5'-N-ethylcarboxamide adenosine ([$^3$H]-NECA) to the membranes. Still more specifically, the dissociation constant ($K_D$) and the maximum number of binding sites ($B_{max}$) were obtained from the results of the saturation binding test of the radioligand ([$^3$H]-CHA or [$^3$H]-NECA) to the above respective membranes; the results were treated by the method of least squares, utilizing a computer program, followed by subjecting to the Scatchard analysis (linear data conversion). On the other hand, the concentration ($IC_{50}$) of the test compound which can substitute 50% of the specific binding of the radioligand having the above concentration was determined from the substitution curve obtained from the results of the test in which the test compounds with various concentrations were incubated. The above-obtained data were applied to the equation of Cheng and Prusoff, presented in Biochem. Pharmacol., 22, 3099 (1973), thereby finally obtaining the affinity constants (Ki). (See "Neurotransmitter and Receptor Binding". pp. 83-119, Seiwa Shoten Kabushiki Kaisha (Sep. 15, 1987).)

The selectivity for $A_1$ and $A_2$ receptors was obtained by calculating the ratio of the Ki value in terms of $A_2$ receptors to that in terms of $A_1$ receptors ($A_1/A_2$).

The results are shown in Table 2.

TEST 2

Effect on Blood Pressure and Heart Rate in SHR

Male spontaneously hypertensive rats (SHRs) were anesthetized with urethane and α-chloralose. The blood pressure of the rats was measured with a pressure transducer through a polyethylene cannula inserted into the left carotid artery. The heart rate was monitored with a cardiotachometer triggered by the arterial pressure pulse. From 0.03 to 100 μg/kg of the test compound was administered to the rats through the femoral veins in a cumulative manner with a common ratio of 3 at an interval of 5 minutes. The blood pressure and the heart rate of the rats were measured 5 minutes after the respective administrations, and the maximum values thereof were determined.

The amount of the test compound ($ED_{30}$) which can make a 30 percent decrease in the initial blood pressure of each SHR, and the amount of the test compound ($ED_{10}$) which can make a 10 percent decrease in the initial heart rate of each SHR were respectively determined from the above-obtained data. Effects of the test compounds on the blood pressure and the heart rate were compared in terms of the $ED_{30}$ and $ED_{10}$ values. The results are also shown in Table 2.

TABLE 2

| Test Compound | | | | Affinity for Adenosine Receptors | | | Blood Pressure | Heart Rate | |
|---|---|---|---|---|---|---|---|---|---|
| | | | | $A_1$ | $A_2$ | | $ED_{30}$ | $ED_{10}$ | |
| Compound No. | n | m | R | (nM) | (nM) | $A_1/A_2$ | (μg/kg) | (μg/kg) | $ED_{10}/ED_{30}$ |
| 18 | 1 | 4 | H | 162 | 2.3 | 69.7 | 0.054 | >100 | >1851 |
| 26 | 1 | 5 | H | 208 | 6.5 | 32.0 | 0.126 | >100 | >793 |
| 29 | 0 | 5 | OH | 21 | 0.9 | 24.6 | 0.014 | 3.29 | 235 |
| 45 | 0 | 7 | OH | 56 | 1.9 | 29.5 | 0.012 | 14.78 | 1231 |
| 2-Octynyladenosine* | | | | 134 | 11.0 | 12.1 | 0.250 | 64.50 | 258 |

*Control Compound

As shown in Table 2, from the comparison of the affinities (Ki) for $A_1$ and $A_2$ receptors between the compounds of the present invention and the control, it has been found that the $A_1/A_2$ ratios of the compounds of the present invention are higher than that of the control compound. Namely, the data show that the selectivity for $A_2$ receptors can be enhanced when the alkynyl group of the control compound which is a linear carbon chain and positioned at the 2 position of the adenine ring is substituted with the alkynyl group of the present invention having a cycloalkyl group.

From the comparison of the ratio of the amount of the compound which can make a 10 percent decrease in the heart rate of SHR to that of the compound which can make a 30 percent decrease in the blood pressure of SHR, that is, the $ED_{10}/ED_{30}$ ratio, between the compounds of the present invention and the control compound, it has been found that the compounds of the present invention tend to have higher ratios. This means that the compounds of the present invention can satisfactorily lower the blood pressure even when they are dosed in such a small amount that the heart rate is little affected.

As described above, the compounds of the present invention have selectivity for $A_2$ receptors higher than that of the known 2-alkynyladenosine, and exhibit an excellent circulation ameliorating effect such as a vasodepressor activity without seriously affecting the heart rate.

Other features of this invention will become apparent from the following description of exemplary embodiments, which are presented for illustration of the invention and are not intended to limit the scope thereof.

EXAMPLE 1

2-(Cyclohexylethynyl)adenosine (Compound No. 25)

1.95 g (5 mmol) of 2-iodoadenosine was dissolved in 20 ml of N,N-dimethylformamide (DMF), to which were added 0.18 g of bis(triphenylphosphine)palladium dichloride, 0.1 g of cuprous iodide, 2.8 ml of triethylamine and 0.8 ml of cyclohexylacetylene. The resulting mixture was stirred at a temperature of 90° C. for two hours. The reaction solution after being allowed to cool, was concentrated to dryness. The residue obtained was dissolved in chloroform, into which was vigorously introduced hydrogen sulfide gas over one minute. The solution was then dried under reduced pressure. The residue was purified by silica gel column chromatography, followed by recrystallization from ethanol-water, thereby obtaining 1.11 g (2.97 mmol) of crystalline 2-(cyclohexylethynyl)adenosine (yield: 59%).

Melting Point [mp]: 135°–141° C. (Recrystallized from EtOH-H$_2$O).

Infrared Absorption Spectrum [IR] (KBr, cm$^{-1}$): 2220 (acetylene).

Nuclear Magnetic Resonance Spectrum: [$^1$H-NMR] (400 MHz, DMSO-d$_6$).

δppm: 1.29–1.84 (10H, m, cyclohexyl), 2.61 (1H, m, CH—C≡C—), 3.54–3.68 (2H, m, H-5'), 3.95 (1H, m, H-4'), 4.12 (1H, dd, H-3'), 4.52 (1H, dd, H-2'), 5.86 (1H, d, H-1', J=5.86 Hz), 7.43 (2H, brs, NH$_2$), 8.39 (1H, s, H-8), Ultraviolet Absorption Spectrum [UV] [nm (ε)]: H$_2$O: λmax 285 (sh), 270 (14,700). λmin 247 (7,100). 50 mM HCl: λmax 294 (12,000), 271 (15,800). λmin 283 (11,400), 247 (6,800). 50 mM NaOH: λmax 285 (sh), 270 (14,700) λmin 247 (7,400).

Elementary Analysis (for C$_{18}$H$_{23}$N$_5$O$_4$.H$_2$O): Calculated (%): C, 55.23; H, 6.44; N, 17.89; Found (%): C, 55.30; H, 6.46; N, 17.72.

EXAMPLE 2

2-[(1-Hydroxycyclohexane-1-yl)ethynyl]adenosine (Compound No. 29)

The procedure of Example 1 was repeated except that 1.14 g (2.9 mmol) of 2-iodoadenosine was used as the starting compound, that the cyclohexylacetylene was replaced by 1-ethynyl-1-cyclohexanol, and that the reaction was carried out at a temperature of 100° C. for one hour, respectively, whereby 0.91 g (2.3 mmol) of crystalline 2-[(1-hydroxycyclohexane-1-yl)ethynyl]adenosine was obtained (yield: 79%).

mp: 142°–147° C. (Recrystallized from EtOH-H$_2$O).
IR (KBr, cm$^{-1}$): 2230 (acetylene),
$^1$H NMR (400 MHz, DMSO-d$_6$).

δppm: 1.25–1.87 (10H, m, cyclohexyl), 3.56–3.71 (2H, m, H-5'), 3.97 (1H, m, H-4'), 4.15 (1H, dd, H-3'), 4.50 (1H, dd, H-2'), 5.1 (1H, d, OH), 5.2 (1H, t, OH), 5.4 (1H, d, OH), 5.5 (1H, s, —C≡C—C—OH), 5.89 (1H, d, H-1', J=5.86 Hz), 7.4 (2H, s, NH$_2$), 8.39 (1H, s, H-8).

UV [nm (ε)]: H$_2$O: λmax 287 (sh), 270 (14,400) λmin 246 (7,100). 50 mM HCl: λmax 294 (10,800), 271 (15,600), λmin 284 (10,300), 247 (7,300), 50 mM NaOH: λmax 287 (sh), 270 (14,000), λmin 247 (7,400).

Elementary Analysis (for C$_{18}$H$_{23}$N$_5$O$_5$.H$_2$O): Calculated (%): C, 53.06; H, 6.18; N, 17.19; Found (%): C, 53.22; H, 6.23; N, 17.01.

EXAMPLE 3

2-(3-cyclopentyl-1-propynyl)adenosine Compound No. 18)

The procedure of Example 1 was repeated except that 1.56 g (3.98 mmol) of 2-iodoadenosine was used as the starting compound and that the cyclohexylacetylene was replaced by 3-cyclopentylpropyne, whereby 1.05 g (2.8 mmol) of crystalline 2-(3-cyclopentyl-1-propynyl)adenosine was obtained (yield: 70.3%).

mp: 125°–127° C. (Recrystallized from EtOH-H$_2$O).
IR KBr, cm$^{-1}$): 2230 (acetylene).
$^1$H-NMR (400 MHz, DMSO-d$_6$).

δppm: 1.29–1.84, 2.10 (9H, m, cyclopentyl), 2.40 (2H, d, CH$_2$C≡C), 3 55–3.71 (2H, m, H-5'), 3.98 (1H, m, H-4'), 4.15 (1H, dd, H-3'), 4.53 (1H, dd, H-2'), 5.12 (1H, d, OH), 5.25 (1H, dd, OH), 5.41 (1H, d, OH), 5.88 (1H, d, H-1', J=5.86 Hz), 7.36 (2H, s, NH$_2$), 8.39 (1H, s, H-8).

UV [nm (ε)]: H$_2$O: λmax 286 (sh), 271 (14,900). λmin 246 (6,800). 50 mM HCl: λmax 293 (12,000), 272 (16,700), λmin 284 (11,600), 248 (6,600). 50 mM NaOH: λmax 286 (sh), 271 (14,900), λmin 247 (7,200).

Elementary Analysis (for C$_{18}$H$_{23}$N$_5$O$_4$.2/3H$_2$O): Calculated (%): C, 56.09; H, 6.36; N, 18.17; Found (%): C, 56.30; H, 6.29; N, 17.90.

EXAMPLE 4

2-[(1-Hydroxycyclopentane-1-yl)ethynyl]adenosine (Compound No. 21)

4.0 g (7.4 mmol) of 9-(2,3,5-tri-O-acetyl-β-D-ribofuranosyl)-6-chloro-2-iodopurine, 190 mg (0.27 mmol) of bis(triphenylphosphine)palladium dichloride and 28 mg (0.15 mmol) of cuprous iodide were suspended in 30 ml of 1,4-dioxane. To the suspension were added 2.0 ml of triethylamine and 0.98 (8.9 mmol) of 1-ethynyl-1-cyclopentanol, followed by reaction at room temperature for 10 hours with stirring.

After the reaction was completed, the reaction solution was concentrated, and to the residue obtained was added 200 ml of chloroform. The resulting solution was distributed and washed several times with an aqueous solution of disodium EDTA (ethylenediaminetetraacetate) and a brine to remove copper ions therefrom. The organic phase was concentrated and then subjected to silica gel column chromatography. From the fraction eluted with an eluent (chloroform:ethyl acetate=2:1) was obtained 2.5 g of 9-(2,3,5-tri-O-acetyl-β-D-ribofuranosyl)-6-chloro-2-[(1-hydroxycyclopentane-1-yl)ethynyl]purine as a viscous substance (yield: 64.6%).

1H-NMR (400 MHz, DMSO-d$_6$).

δppm: 8.28 (1H, s, H-8), 6.22 (1H, d, H-1'), 5.90 (1H, t, H-2'), 5.73–5.71 (1H, m, H-3'), 4.51–4.43 (3H, m, H-4', H-5'), 2.85 (1H, s, OH), 2.18 (3H, s, acetyl), 2.13 (3H, s, acetyl), 2.09 (3H, s, acetyl), 1.93–1.67 (8H, m, cyclopentyl).

To 2.5 g (4.8 mmol) of 9-(2,3,5-tri-O-acetyl-β-D-ribofuranosyl)-6-chloro-2-[(1-hydroxycyclopentane-1-yl)ethynyl]purine was added 90 ml of a 2:1 (v/v) mixture of dioxane and concentrated aqueous ammonia. The mixture placed in a sealed tube was heated to a temperature of 70° C. for 20 hours for the purposes of both amination and removal of the acetyl group.

After the reaction was completed, the reaction solution was concentrated and subjected to silica gel column chromatography. 2-[(1-Hydroxycyclopentane-1-yl)ethynyl]adenosine was obtained from the fraction eluted with an eluent (chloroform:methanol=7:1). The adenosine derivative thus obtained was then recrystallized from ethanol-water, whereby 0.93 g of the captioned compound was obtained in crystalline form (yield: 51.7%).

mp: 138°–144° C. (Recrystallized from EtOH-H$_2$O).
IR (KBr, cm$^{-1}$): 2232 (acetylene).
$^1$H-NMR (400 MHz, DMSO-d$_6$).

δppm: 8.41 (1H, s, H-8), 7.43 (2H, s, NH$_2$), 5.87 (1H, d, H-1'), 5.46 (1H, d, OH), 5.41 (1H, s, —C≡C—C—OH), 5.18–5.15 (2H, m, OH ×2), 4.48 (1H, dd, H-2'), 4.11 (1H, dd, H-3'), 3.95 (1H, dd, H-4'), 3.69–3.53 (2H, m, H-5'), 1.93–1.66 (8H, m, cyclopentyl).

UV [nm (ε)]: H$_2$O: λmax 270 (14,900); λmin 248 (8,800). 50 mM HCl: λmax 271 (16,300) λmin 248 (8,600) 50 mM NaOH: λmax 270 (15,000) λmin 247 (8,400)

Elementary Analysis (for C$_{17}$H$_{21}$N$_5$O$_5$.H$_2$O) Calculated (%): C, 51.90; H, 5 89; N, ]7.80 Found (%): C, 52.00; H, 5.83; N, 17.54

EXAMPLE 5

5'-O-benzyl-2-[(1-hydroxycyclohexane-1-yl-ethynyl-]adenosine (5'-O-benzyl derivative of Compound No. 21):

Synthesis of
5'-O-benzyl-2-iodo-2',3'-O-isopropylideneadenosine 433 mg (1.0 mmol) of 2-iodo-2',3'-O-isopropylideneadenosine was dissolved in 20 ml of THF, to which was added 150 mg (3.8 mmol) of 60% sodium hydride. The resulting mixture was stirred at room temperature for 30 minutes. 190 mg (1.1 mmol) of benzylbromide was then added to the mixture, and the mixture was stirred at room temperature all night. After addition of water, the reaction mixture was extracted with chloroform. The extracted phase was washed with water and dried over anhydrous sodium sulfate, and the solvent was removed by distillation under reduced pressure. The residue was purified by silica gel column chromatography, thereby obtaining 120 mg of the captioned compound as a foamy substance (yield: 33.5%).

$^1$H-NMR (400 MHz, CDCl$_3$).

δppm: 7.86 (1H, s, H-8), 7.33–7.25 (5H, m, H-φ), 6.10 (1H, d, H-1'), 6.01 (2H, s, NH$_2$), 5.24 (1H, dd, H-2'), 5.00 (1H, dd, H-3'), 4.56–4.46 (3H, m, φ-CH$_2$, H-4'), 3.73–3.63 (2H, m, H-5'), 1.61 (3H, s, methyl), 1.39 (3H, s, methyl).

(2) Synthesis of
5'-O-benzyl-2-[(1-hydroxycyclohexane-1-yl)ethynyl]-2',3'-O-isopropylideneadenosine 230 mg (0.44 mmol) of 5'-O-benzyl-2-iodo-2',3'-O-isopropylideneadenosine was dissolved in 10 ml of DMF, to which were added 30 mg (10 mol %) of bis(triphenylphosphine)palladium dichloride, 70 mg (0.56 mmol) of 1-ethynyl-1-cyclohexanol, 8 mg (10 mol %) of cuprous iodide and 0.5 ml of triethylamine. The resulting mixture was stirred at a temperature of 70° C. for 20 hours in an argon atmosphere, and then the solvent was distilled off under reduced pressure. The residue was distributed with chloroform and an aqueous EDTA.2Na solution. The chloroform phase was washed with water and dried over anhydrous sodium sulfate, and the solvent was removed by distillation under reduced pressure. The residue was subjected to silica gel column chromatography, whereby 190 mg of the captioned compound was obtained from the fraction eluted with an eluent.(chloroform:methanol=50:1) (yield: 82.6%).

$^1$H-NMR (400 MHz, CDCl$_3$).

δppm: 8.03 (1H, s, H-8), 7.31–7.22 (5H, m, H-φ), 6.20 (1H, d, H-1'), 5.63 (2H, brs, NH$_2$), 5.24 (1H, dd, H-2'), 5.01 (1H, dd, H-3'), 4.55–4.46 (3H, m, φ-CH$_2$, H-4'), 3.70–3.64 (2H, m, H-5'), 1.62 (3H, s, methyl), 1.39 (3H, s, methyl), 2.04–1.39 (10H, m, cyclohexyl).

(3) Synthesis of
5'-O-benzyl-2-[(1-hydroxycyclohexane-1-yl)ethynyl-]adenosine:

190 mg (0.37 mmol) of 5'-O-benzyl-2-[(1-hydroxycyclohexane-1-yl)ethynyl]-2',3'-O-isopropylideneadenosine was dissolved in 2 ml of trifluoroacetic acid, to which was added 0.5 ml of water. The resulting mixture was stirred at room temperature for 1 hour. The solvent was distilled off under reduced pressure, and the residue was dissolved in chloroform. The solution obtained was washed with a saturated aqueous solution of sodium hydrogencarbonate and water and dried over anhydrous sodium sulfate, and the solvent was removed by distillation under reduced pressure. The residue was subjected to silica gel column chromatography. The fraction eluted with an eluent (chloroform:methanol=10:1) was recrystallized from ether, whereby 46 mg of the captioned compound was obtained in crystalline form (yield: 26.3%).

mp: 179°–180° C. (Recrystallized from EtOH-H$_2$O).
IR (KBr, cm$^{-1}$): 2220 (acetylene).
$^1$H-NMR (400 MHz, DMSO-d$_6$).

δppm: 8.28 (1H, s, H-8), 7.43 (2H, s, NH$_2$), 7.37–7.29 (5H, m, H-φ), 5.89 (1H, d, H-1'), 5.56 (1H, s, —C≡C—C—OH), 5.55 (1H, d, OH), 5.31 (1H, d, OH), 4.54–4.52 (3H, m, φ-CH$_2$, H-2'), 4.16 (1H, dd, H-3'), 4.08 (1H, dd, H-4'), 3.75–3.64 (2H, m, H-5'), 1.81–1.26 (10H, m, cyclohexyl).

Elementary Analysis (for C$_{25}$H$_{29}$N$_5$O$_5$): Calculated (%) C, 62.61; H, 6.10; N, 14.60, Found (%): C, 62.56; H, 6.11; N, 14.48.

EXAMPLE 6

Synthesis of Compounds Having Formula [I]
(Compounds Nos. 17, 19, 26, 27, 28, 37 and 45)

(1) Synthesis of Intermediate [V]

9-(2,3,5-Tri-O-acetyl-β-D-ribofuranosyl)-6-chloro-2-iodopurine having formula [IV], bis(triphenylphosphine)palladium dichloride (0.05 equivalent) serving as a catalyst and cuprous iodide (0.05 equivalent) serving as a copper compound were suspended in a solvent, 1,4-dioxane. To the suspension were added triethylamine and an acetylene compound represented by formula [III] having a cycloalkylalkynyl chain corresponding to a desired compound. The suspension was reacted at room temperature for 12 hours with stirring.

After the reaction was completed, the reaction solution was concentrated, and the residue was dissolved in 200 ml of ethyl acetate. The solution was distributed and washed several times with an aqueous EDTA.2Na solution and a brine to remove copper ions therefrom. The organic phase was concentrated and then subjected to silica gel column chromatography. 9-(2,3,5-Tri-O-acetyl-β-D-ribofuranosyl)-6-chloro-2-cycloalkylalkynylpurine having formula [V] was obtained from the fraction eluted with an eluent (chloroform:ethyl acetate) as an oily substance.

In the above reaction process, the type and amount of the starting compounds used, the amount of the reagents employed, the type, amount and yield of the intermediates produced, and the formulation of the eluents employed for purification using silica gel column chromatography are shown in Table 3.

(2H, t, —C≡C—CH$_2$—), 4.41 (2H, d, H-5'), 4.47 (1H, dd, H-4'), 5.57 (1H, dd, H-3'), 5.80 (1H, t, H-2'), 6.32 (1H, d, H-1'), 8.31 (1H, s, H-8).

Intermediate (vi)

δppm: 1.63–2.04 (1H, m, cycloheptyl), 2.10 (3H, s, acetyl), 2.12 (3H, s, acetyl), 2.17 (3H, s, acetyl), 2.82 (1H, s, —C≡C—C—OH), 4.44–4.52 (3H, m, H-5',

TABLE 3

| | | | Starting Compound | | Intermediate (Formula [V]) | | Reagent (Amount) | | | Formulation of Eluent |
|---|---|---|---|---|---|---|---|---|---|---|
| n | m | R | Amount of Compound [IV] (g) ((mmol)) | Amount of Compound [III] (g) | No. | Production Amount (g) (Yield (%)) | Catalyst mg | Copper Compound (mg) | Solvent (ml) | Triethyl- amine (ml) | Chloroform: Ethyl acetate |
| 0 | 4 | H | 5.38 (10) | 1.1 | (i) | 4.8 (95) | 350 | 95 | 50 | 2.1 | 2:1 |
| 2 | 4 | H | 4.00 (7.4) | 1.2 | (ii) | 3.3 (84) | 260 | 70 | 40 | 1.6 | 2:1 |
| 1 | 5 | H | 5.38 (10) | 1.5 | (iii) | 5.6 (100) | 350 | 95 | 50 | 2.1 | 2:1 |
| 2 | 5 | H | 5.38 (10) | 1.7 | (iv) | 5.5 (100) | 350 | 95 | 50 | 2.1 | 2:1 |
| 3 | 5 | H | 5.38 (10) | 1.8 | (v) | 2.7 (48) | 350 | 95 | 50 | 2.1 | 3:1 |
| 0 | 6 | OH | 4.00 (7.4) | 1.3 | (vi) | 3.9 (71) | 260 | 70 | 40 | 1.6 | 2:1–1:1 |
| 0 | 7 | OH | 5.38 (10) | 1.7 | (vii) | 5.5 (98) | 350 | 95 | 50 | 2.1 | 2:1–1:1 |

The identification data of the intermediates obtained by $^1$H-NMR (400 MHz, CDCl$_3$) are shown below.

Intermediate (i)

δppm: 1.24–1.84 (8H, m, cyclopentyl), 2.08 (3H, s, acetyl), 2.16 (3H, s, acetyl), 2.17 (3H, s, acetyl), 2.88–2.92 (1H, m, —C≡C—CH<), 4.41 (2H, d, H-5'), 4.46 (1H, dd, H-4'), 5.58 (1H, dd, H-3'), 5.81 (1H, t, H-2'), 6.32 (1H, d, H-1'), 8.30 (1H, s, H-8).

Intermediate (ii)

δppm: 1.10–1.97 (11H, m, C$_5$H$_9$CH$_2$), 2.08 (3H, s, acetyl), 2.16 (3H, s, acetyl), 2.17 (3H, s, acetyl), 4.41 (2H, d, H-5'), 4.46 (1H, dd, H-4'), 5.57 (1H, dd, H-3'), 5.81 (1H, t, H-2'), 6.32 (1H, d, H-1'), 8.31 (1H, s, H-8).

Intermediate (iii)

δppm: 1.05–1.92 (11H, m, cyclohexyl), 2.08 (3H, s, acetyl), 2.16 (3H, s, acetyl), 2.17 (3H, s, acetyl), 2.38 (2H, d, —C≡C—CH$_2$—), 4.41 (2H, d, H-5'), 4.47 (1H, dd, H-4'), 5.58 (1H, dd, H-3'), 5.81 (1H, t, H-2'), 6.31 (1H, d, H-1'), 8.30 (1H, s, H-8).

Intermediate (iv)

δppm: 0.88–1.77 (13H, m, C$_6$H$_{11}$CH$_2$—), 2.08 (3H, s, acetyl), 2.16 (3H, s, acetyl), 2.17 (3H, s, acetyl), 2.49 (2H, t, —C≡C—CH$_2$—), 4.41 (2H, d, H-5'), 4.46 (1H, dd, H-4'), 5.57 (1H, dd, H-3'), 5.80 (1H, t, H-2'), 6.32 (1H, d, H-1'), 8.31 (1H, s, H-8).

Intermediate (v)

δppm: 0.84–1.72 (15H, m, C$_6$H$_{11}$CH$_2$CH$_2$), 2.08 (3H, s, acetyl), 2.16 (3H, s, acetyl), 2.17 (3H, s, acetyl), 2.46

H-4'), 5.75 (1H, dd, H-3'), 5.90 (1H, t, H-2'), 6.21 (1H, d, H-1'), 8.27 (1H, s, H-8).

Intermediate (vii)

δppm: 1.51–2.14 (14H, m, cyclooctyl), 2.10 (3H, s, acetyl), 2.12 (3H, s, acetyl), 2.17 (3H, s, acetyl), 2.65 (1H, s, —C≡C—C—OH), 4.42–4.51 (3H, m, H-4', H-5'), 5.75 (1H, dd, H-3'), 5.89 (1H, t, H-2'), 6.20 (1H, d, H-1'), 8.27 (1H, s, H-8).

(2) Synthesis of Compound Having Formula [I]

9-(2,3,5-Tri-O-acetyl-β-D-ribofuranosyl)-6-chloro-2-cycloalkylalkynylpurine having formula [V] was dissolved in 120 ml of 1,4-dioxane, to which was added 60 ml of concentrated aqueous ammonia. The resulting mixture placed in a sealed tube was heated to a temperature of 70° C. for 18 hours for the purposes of both amination and removal of the acetyl group.

After the reaction was completed, the reaction solution was concentrated and subjected to silica gel column chromatography. 2-Cycloalkylalkynyladenosine having formula [I] was obtained from the fraction eluted with an eluent (chloroform:methanol) as a crude crystalline or foamy substance.

In the above reaction process, the type and amount of the starting compounds, i.e., the intermediates obtained in the above (1), employed, the type, amount and yield of the end products, and the formulation of the eluents employed for purification using silica gel column chromatography are shown in Table 4.

TABLE 4

| | | | Starting Compound (Intermediate: Formula [V]) Amount (g) | End Compound (Formula [I]) | | Formulation of Eluent Chloroform:Methanol |
|---|---|---|---|---|---|---|
| n | m | R | | Compound No. | Production Amount (g) (Yield (%)) | |
| 0 | 4 | H | 4.8 | 17 | 2.3 (67) | 10:1 |
| 2 | 4 | H | 2.8 | 19 | 1.7 (85) | 10:1 |

TABLE 4-continued

| | | | Starting Compound (Intermediate: Formula [V]) | End Compound (Formula [I]) | | Formulation of Eluent Chloroform:Methanol |
|---|---|---|---|---|---|---|
| n | m | R | Amount (g) | Compound No. | Production Amount (g) (Yield (%)) | |
| 1 | 5 | H | 5.6 | 26 | 2.6 (67) | 10:1 |
| 2 | 5 | H | 5.5 | 27 | 2.8 (70) | 10:1 |
| 3 | 5 | H | 2.7 | 28 | 1.1 (55) | 10:1 |
| 0 | 6 | OH | 3.4 | 37 | 1.6 (65) | 5:1 |
| 0 | 7 | OH | 5.5 | 45 | 2.3 (56) | 5:1 |

The identification data of the end products are shown below.

Compound No. 17 mp: 127°–133° C. (Recrystallized from EtOH-H$_2$O)
IR (KBr, cm$^{-1}$): 2232 (acetylene)
$^1$H-NMR (400 MHz, DMSO-d$_6$)
δppm: 1.56–1.99 (8H, m, cyclopentyl), 2.84 (1H, m, —C≡C—CH<), 3.55–3.65 (2H, m, H-5'), 3.95 (1H, d, H-4'), 4.12 (1H, dd, H-3'), 4.51 (1H, dd, H-2'), 5.18 (1H, d, OH), 5.22 (1H, dd, OH), 5.45 (1H, d, OH), 5.85 (1H, d, H-1'), 7.41 (2H, brs, NH$_2$), 8.38 (s, 1H, H-8).
Elementary Analysis (for C$_{17}$H$_{21}$N$_5$O$_4$.1H$_2$O): Calculated (%): C, 54.10; H, 6.14; N, 18.56, Found (%): C, 54.15; H, 6.15; N, 18.64.

Compound No. 19 mp: 108°–114° C. (Recrystallized from EtOH-H$_2$O)
IR (KBr, cm$^{-1}$): 2236 (acetylene)
$^1$H-NMR (400 MHz, DMSO-d$_6$)
δppm: 1.09–1.95 (11H, m, C$_5$H$_9$CH$_2$), 2.40 (2H, t, —C≡C—CH$_2$—), 3.53–3.68 (2H, m, H-5'), 3.95 (1H, dd, H-4'), 4.12 (1H, dd, H-3+) 4.53 (1H, dd, H-2'), 5.16 (1H, d, OH), 5.21 (1H, t, OH), 5.44 (1H, d, OH), 5.85 (1H, d, H-1'), 7.41 (1H, brs, NH$_2$), 8.38 (s, 1H, H-8).

Compound No. 26 mp: 97°–103° C. (Recrystallized from EtOH-H$_2$O).
IR (KBr, cm$^{-1}$): 2236 (acetylene).
$^1$H-NMR (400 MHz, DMSO-d$_6$).
δppm: 1.03–1.83 (11H, m, cyclohexyl), 2.31 (2H, d, —C≡C—CH$_2$—), 3.53–3.68 (2H, m, H-5'), 3.95 (1H, dd, H-4'), 4.12 (1H, dd, H-3'), 4.53 (1H, dd, H-2'), 5.18 (1H, d, OH), 5.23 (1H, dd, OH), 5.45 (1H, d, OH), 5.85 (1H, d, H-1'), 7.41 (2H, brs, NH$_2$), 8.38 (s, 1H, H-8),

Compound No. 27 mp: 104°–111° C. (Recrystallized from EtOH-H$_2$O).
IR (KBr, cm$^{-1}$): 2240 (acetylene).
$^1$H-NMR (400 MHz, DMSO-d$_6$).
δppm: 0.87–1.76 (13H, m, C$_6$H$_{11}$CH$_2$), 2.41 (2H, t, —C≡C—CH$_2$—), 3.57–3.68 (2H, m, H-5'), 3.95 (1H, dd, H-4'), 4.12 (1H, d, H-3'), 4.53 (1H, dd, H-2'), 5.16 (1H, d, OH), 5.22 (1H, brs, OH), 5.44 (1H, d, OH), 5.85 (1H, d, H-1'), 7.41 (2H, brs, NH$_2$), 8.38 (s, 1H, H-8).
Elementary Analysis (for C$_{20}$H$_{27}$N$_5$O$_4$.2/3H$_2$O): Calculated (%): C, 58.09; H, 6.91; N, 16.94; Found (%): C, 58.09; H, 6.80; N, 17.06.

Compound No. 28 mp: 117°–127° C. (Recrystallized from EtOH-H$_2$O).
IR (KBr, cm$^{-1}$): 2232 (acetylene).
$^1$.NMR (400 MHz, DMSO-d$_6$).
δppm: 0.86–1.71 (15H, m, C$_6$H$_{11}$CH$_2$CH$_2$), 2.38 (2H, t, —C≡C—CH$_2$—), 3.55–3.68 (2H, m, H-5'), 3.95 (1H, d, H-4'), 4.12 (1H, dd, H-3'), 4.54 (1H, dd, H-2'), 5.18 (1H, d, OH), 5.24 (1H, dd, OH), 5.85 (1H, d, OH), 7.42 (2H, brs, NH$_2$), 8.39 (s, 1H, H-8).
Elementary Analysis (for C$_{21}$H$_{29}$N$_5$O$_4$.1H$_2$O): Calculated (%): C, 58.18; H, 7.21; N, 16.15; Found (%): C, 58.27; H, 7.15; N, 16.17.

Compound No. 37 mp: 128°–140° C. (foam).
IR (KBr, cm$^{-1}$): 2228 (acetylene).
$^1$H-NMR (400 MHz, DMSO-d$_6$).
δppm: 1.49–2.00 (12H, m, cycloheptyl), 3.53–3.69 (2H, m, H-5'), 3.95 (1H, dd, H-4') 4.11 (1H, dd, H-3'), 4.50 (1H, dd, H-2'), 5.14–5.17 (2H, m, OH×2), 5.41 (1H, s, —C≡C—C—OH), 5.45 (1H, d, OH), 5.87 (1H, d, H-1'), 7.44 (2H, brs, NH$_2$), 8.42 (s, 1H, H-8).

Compound No. 45 mp: 132°–142° C. (foam).
IR (KBr, cm$^{-1}$): 2232 (acetylene).
$^1$H-NMR (400 MHz, DMSO-d$_6$).
δppm: 1.45–1.93 (14H, m, cyclooctyl), 3.54–3.68 (2H, m, H-5'), 3.95 (1H, dd, H-4'), 4.12 (1H, dd, H-3'), 4.50 (1H, t, H-2'), 5.87 (1H, d, H-1'), 7.45 (2H, brs, NH$_2$), 8.41 (s, 1H, H-8).
Elementary Analysis (for C$_{20}$H$_{27}$N$_5$O$_5$.1.5H$_2$O): Calculated (%): C, 54.04; H, 6.80; N, 15.76; Found (%): C, 54.23; H, 6.80; N, 15.49.

EXAMPLE 7

The following ingredients were thoroughly mixed to give a uniform mixture. 200 mg of the mixture was charged in a hard capsule to obtain a capsulated preparation.

| | |
|---|---|
| 2-(3-Cyclopentyl-1-propynyl)adenosine (Compound No. 18) | 25 mg |
| Potato starch | 150 mg |
| Light anhydrous silicate | 50 mg |
| Magnesium stearate | 10 mg |
| Lactose | 765 mg |
| Total | 1000 mg |

EXAMPLE 8

A tablet was prepared using the following ingredients:

| | |
|---|---|
| 2-[(1-Hydroxycyclohexane-1-yl)ethynyl]-adenosine (Compound No. 29) | 25 mg |
| Potato starch | 150 mg |

| | |
|---|---|
| Crystalline cellulose | 60 mg |
| Light anhydrous silicate | 50 mg |
| Hydroxypropyl cellulose | 30 mg |
| Magnesium stearate | 15 mg |
| Lactose | 670 mg |
| Total | 1000 mg |

2-[(1-Hydroxycyclohexane-1-yl)ethynyl]adenosine, lactose, potato starch, crystalline cellulose and light anhydrous silicate were mixed, to which was added a 10% methanol solution of hydroxypropyl cellulose. The resulting mixture was kneaded, and then extruded from a screen with 0.8-mm mesh, thereby obtaining granules. The granules were dried and then subjected to compression molding together with magnesium stearate, thereby obtaining tablets, each weighing 200 mg.

EXAMPLE 9

25 mg of 2-(cyclohexylethynyl)adenosine (Compound No. 25) was dissolved in 10 ml of propylene glycol, and the resulting solution was subjected to aseptic filtration. 0.2 ml of the solution was charged in an ampoule.

EXAMPLE 10

The following ingredients were heated to a temperature of 60° C. to melt them and thoroughly mixed to give a uniform mixture. The mixture was poured into a plastic mold, and then cooled, thereby obtaining suppositories, each weighing 1 g.

| | |
|---|---|
| 2-(3-Cyclopentyl-1-propynyl)-adenosine (Compound No. 18) | 25 mg |
| Polyethylene glycol 1500 | 3000 mg |
| Polyethylene glycol 6000 | 1975 mg |
| Total | 5000 mg |

What is claimed is:

1. A 2-substituted adenosine derivative having the following formula [I]

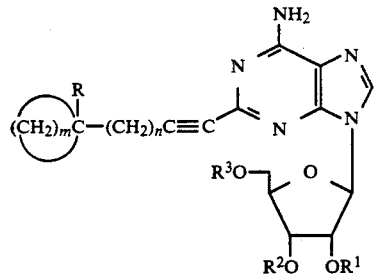

wherein R represents a hydrogen atom or a hydroxyl group,
m is an integer of 2 to 7,
n is 0 or an integer of 1 to 3, and
$R^1$, $R^2$ and $R^3$, which may be same or different, each independently represent (1) a hydrogen atom, (2) a hydroxy protective group selected from the group consisting of acetyl, chloroacetyl, dichloroacetyl, trifluoroacetyl, methoxyacetyl, propionyl, n-butyryl, (E)-2-methylbutenoyl, isobutyryl, pentanoyl, benzoyl, o-(dibromomethyl)benzoyl, o-(methoxycarbonyl)benzoyl, p-phenylbenzoyl, 2,4,6-trimethylbenzoyl, p-toluoyl, p-anisoyl, p-chlorobenzoyl, p-nitrobenzoyl, α-naphthoyl, benzyl, phenethyl, 3-phenylpropyl, p-methoxybenzyl, p-nitrobenzyl, o-nitrobenzyl, p-halobenzyl, p-cyanobenzyl, diphenylmethyl, triphenylmethyl, α- or β-naphthylmethyl, α-naphthyldiphenylmethyl, trimethylsilyl, triethylsilyl, dimethylisopropylsilyl, isopropyldimethylsilyl, methyl-di-t-butylsilyl, t-butyldimethylsilyl, t-butyldiphenylsilyl, triisopropylsilyl, tetraisopropyldisiloxanyl, methoxymethyl, ethoxymethyl, isopropylidene, ethylidene, propylidene, benzylidene and methoxymethylidene, or (3) a phosphoric acid residue represented by the following formula [A] or [B]:

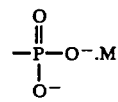 [A]

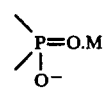 [B]

wherein
M represents one or more cations having a positive charge which corresponds to a negative charge of the phosphoric acid residue,
or a salt thereof.

2. The compound as claimed in claim 1, wherein $R^1$, $R^2$ and $R^3$ each are a hydrogen atom, and m is an integer of 4 to 7.

3. A pharmaceutical composition comprising as an active ingredient a 2-substituted adenosine derivative or a pharmaceutically acceptable salt thereof as claimed in claim 1, and a pharmaceutically acceptable carrier.

4. The pharmaceutical composition as claimed in claim 3, wherein $R^1$, $R^2$ and $R^3$ each are a hydrogen atom, and m is an integer of 4 to 7.

5. A method of treating a patient requiring a hypotensor, which comprises administering to said patient a therapeutically effective amount of a hypotensor comprising as an active ingredient an effective amount of a 2-substituted adenosine derivative having the following formula [I]

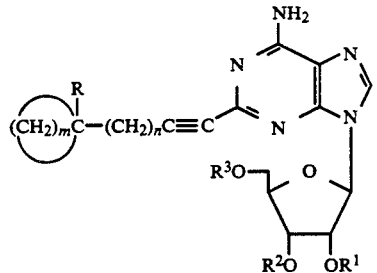

wherein
R represents a hydrogen atom or a hydroxyl group,
m is an integer of 2 to 7,
n is 0 or an integer of 1 to 3, and
$R^1$, $R^2$ and $R^3$, which may be the same or different, each independently represents a hydrogen atom or a hydroxy protective group selected from the group consisting of acetyl, chloroacetyl, dichloroacetyl, trifluoroacetyl, methoxyacetyl, propionyl, n-butyryl, (E)-2-methylbutenoyl, isobutyryl, pentanoyl, benzoyl, o-(dibromomethyl)benzoyl, o-

(methoxycarbonyl)benzoyl, p-phenylbenzoyl, 2,4,6-trimethylbenzoyl, p-toluoyl, p-anisoyl, p-chlorobenzoyl, p-nitrobenzoyl, α-naphthoyl, benzyl, phenethyl, 3-phenylpropyl, p-methoxybenzyl, p-nitrobenzyl, o-nitrobenzyl, p-halobenzyl, p-cyanobenzyl, diphenylmethyl, triphenylmethyl, α- or β-naphthylmethyl, α-naphthyldiphenylmethyl, trimethylsilyl, triethylsilyl, dimethylisopropylsilyl, isopropyldimethylsilyl, methyl-di-t-butylsilyl, t-butyldimethylsilyl, t-butyldiphenylsilyl, triisopropylsilyl, tetraisopropyldisiloxanyl, methoxymethyl, ethoxymethyl, isopropylidene, ethylidene, propylidene, benzylidene and methoxymethylidene, or a pharmaceutically acceptable salt thereof.

* * * * *